_United States Patent_ [19]

Ohba et al.

[11] 4,202,886
[45] May 13, 1980

[54] ANTIBIOTIC SF-1942 SUBSTANCE AND PROCESS FOR PRODUCTION OF THE SAME

[75] Inventors: Kazunori Ohba; Takashi Shomura; Yasuaki Ogawa, all of Yokohama; Takashi Tsuruoka, Kawasaki; Hiroshi Watanabe, Yokohama; Takashi Hisamatsu, Yokohama; Shingo Uchida, Yokohama; Michio Kojima, Tokyo; Shigeharu Inouye, Yokohama, all of Japan

[73] Assignee: Meiji Seika Kaisha, Ltd., Tokyo, Japan

[21] Appl. No.: 902,137

[22] Filed: May 2, 1978

[30] Foreign Application Priority Data

May 2, 1977 [JP] Japan ................................. 52-49896

[51] Int. Cl.² ......................... A61K 35/74; C12P 1/06
[52] U.S. Cl. ....................................... 424/122; 435/169
[58] Field of Search ...................... 195/80 R; 424/122; 435/169

[56] References Cited

U.S. PATENT DOCUMENTS

| | | | |
|---|---|---|---|
| 3,096,243 | 7/1963 | Pansy et al. | 424/122 |
| 3,183,155 | 5/1965 | Camieno et al. | 424/122 |

_Primary Examiner_—Alvin E. Tanenholtz
_Attorney, Agent, or Firm_—Sughrue, Rothwell, Mion, Zinn and Macpeak

[57] ABSTRACT

An antibiotic SF-1942 substance produced by cultivating an SF-1942 substance producing strain of the genus Streptomyces in a nutrient medium under aerobic conditions to produce and accumulate the SF-1942 substance in the nutrient medium and isolating the SF-1942 substance from the fermentation broth followed by purification and a process for the production of the antibiotic SF-1942 substance. The SF-1942 substance is effective as an antimicrobial agent and an antitumor agent against Sarcoma 180 tumor cells in mice.

2 Claims, 2 Drawing Figures

FIG I

ANTIBIOTIC SF-1942 SUBSTANCE AND PROCESS FOR PRODUCTION OF THE SAME

BACKGROUND OF THE INVENTION

It is well known that various microbial species of the genus Streptomyces are capable of producing antibiotics upon cultivation in a nutrient medium containing assimilable carbon and nitrogen sources.

This invention relates to a novel antibiotic, designated an SF-1942 substance, and to a process for producing the same from a stain belonging to the genus Streptomyces.

SUMMARY OF THE INVENTION

According to the present invention, it has now been found that a strain belonging to the genus Streptomyces is capable of producing a novel antibiotic, designated an SF-1942 substance, and the resulting SF-1942 substance can be isolated from the fermentation broth.

The SF-1942 substance of the present invention has not yet been previously reported in the literature in view of its physical and chemical properties and is believed to be a novel substance.

More particularly, in one embodiment, this invention provides a process for producing an antibiotic SF-1942 substance produced by cultivating an SF-1942 substance producing strain in a nutrient medium under aerobic conditions until a substantial amount of an antibiotic SF-1942 substance is accumulated in the nutrient medium and isolating the SF-1942 substance thus obtained from the resulting fermentation broth, and to an antitumor agent, against Sarcoma 180 tumor cells in mice, containing the antibiotic SF-1942 substance.

In another embodiment, this invention provides an antibiotic SF-1942 substance, whose physical and chemical properties are as described in detail hereinbelow.

DETAILED DESCRIPTION OF THE INVENTION

Figure 1:
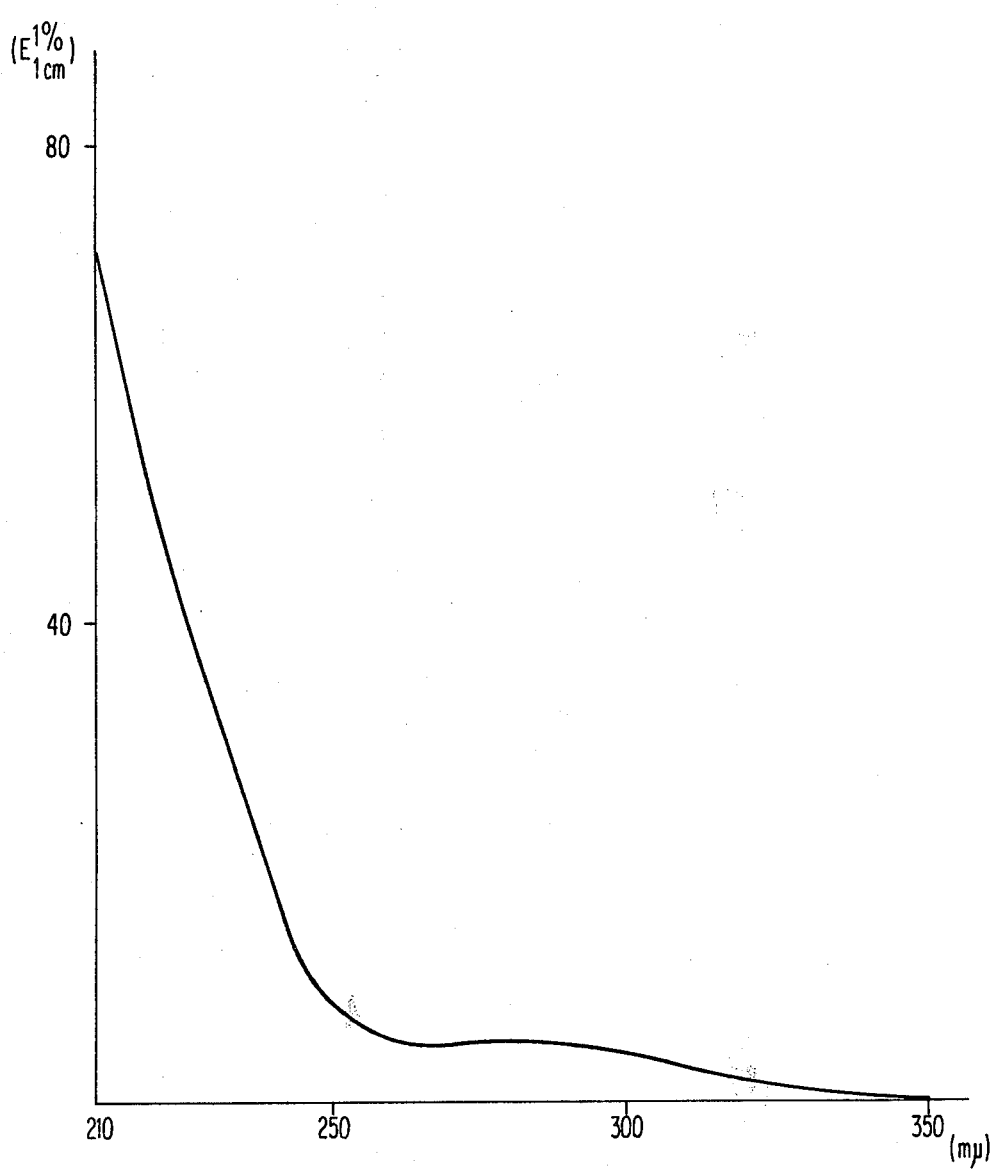
FIG. 1 is a ultraviolet absorption spectrum of the SF-1942 substance as determined at a 1% concentration of the SF-1942 substance in methanol.

An example of the SF-1942 substance producing strain used in the present invention is an SF-1942 strain which was isolated from a soil sample collected in Onomichi-Shi, Hiroshima, Japan.

The characteristics of the SF-1942 strain are as follows.

(I) Morphological Characteristics:

Aerial mycelium is abundantly grown in starch agar, tyrosin agar and other media, with good spore formation. The branching of aerial mycelium is simple and wheel-like branching is not found. The aerial mycelium is relatively short, linear but sometimes loops are formed at the end thereof. No spiral mycelium is found.

Microscopic observation shows that spores have a smooth surface, a cylindrical shape, and a size of 0.5 to 0.7 × 1.0 to 1.2 microns, and generally form a chain of more than about 10 spores.

(II) Culture Characteristics:

The culture characteristics of the SF-1942 strain were observed on various media as shown in Table 1 below at 28° C. The color shown in the parentheses in Table 1 is identified according to the color standard of the Color Harmony Manual, published by Container Corporation of America.

Table 1

| Culture Medium | Growth & Reverse Color | Aerial Mycelium | Soluble Pigment |
|---|---|---|---|
| Sucrose-Nitrate Agar | Medium growth, Pale pinkish yellow brown, | None | Pale pink |
| Glucose-Asparagine Agar | Medium growth, Pale brownish yellow | Gray [e-d] | Not produced |
| Glycerol-Asparagine Agar | Medium growth, Pale grayish yellow | Gray [e] | Not produced |
| Starch Agar | Fair growth, Pinkish gray brown | Abundant, Gray [e-3ig] | Not produced or pale gray pink |
| Oatmeal Agar | Fair growth, Pale brown | Gray [e-2ih] | Pinkish gray brown |
| Yeast Malt Agar | Scant to Medium growth, Wrinkled, Pale yellow | None | Not produced |
| Tyrosine Agar | Fair growth, brown | Abundant, Gray [e] | Not produced |
| Nutrient Agar | Scant growth, Wrinkled, Colorless to pale yellow | None | Not produced |

(III) Physiological Characteristics:

(1) Growth occurs on starch agar medium at a temperature range of 20° to 37° C.
(2) Liquefaction of Gelatin: positive (at 20° C.)
(3) Hydrolysis of Starch: positive (at 28° C.)
(4) Peptonization of Skim Milk: positive (at 28° C.)
 Coagulation of Skim Milk: negative (at 28° C.)
(5) Production of Melamine-like Pigments: negative

(IV) Utilization of Sugars (Pridham & Gottlieb Agar Medium at 28° C.)

(1) Utilizable:
 D-Glucose, D-Fructose, D-Xylose, D-Mannitol, I-Inositol, L-Arabinose, Sucrose, Raffinose
(2) Not utilizable: Rhamnose Summarizing the above-described characteristics, the SF-1942 strain used in the present invention belongs to the genus Streptomyces, and the aerial mycelium is mainly linear and the surface structure of the spores is smooth. On cultivation, the aerial mycelium has a gray color and the reverse color is generally yellowish brown to grayish brown, but is sometimes pinkish depending upon the type of media. No melamine-like pigment is produced, but soluble pigments having a pale yellow to grayish pink color are formed on sucrose-nitrate agar, oatmeal agar and starch agar media.

The SF-1942 strain has been named "Streptomyces sp. SF-1942" and a sample of the culture has been deposited in the Fermentation Research Institute, Agency of Industrial Science and Technology, Ministry of International Trade and Industry of Japan under the accession number, FERM-P No. 3939 and in the American Type Culture Collection (ATCC) under ATCC number 31368.

As a result of a comparative study on the above microbial characteristics with reference to those reported in International Streptomyces Project (ISP) [*International Journal of Systematic Bacteriology*, Vol. 18, pages 69–189, ibid. Vol. 18, pages 279–392 (1968), ibid. Vol. 19, pages 391–512 (1969), and ibid. Vol. 22, pages 265–394 (1972) and with reference to the descriptions reported by Waksman (S.A. Waksman, *The Actinomycetes*, Vol. 2, (1961) and by Hutter (R. Hutter, *Systematik der Streptomyceten*, (1967), it was found that the above SF-1942 strain is considered to be closely related to *Streptomyces griseoluteus*. A direct comparison of the culture characteristics by culturing side-by-side SF-1942 strain and *Streptomyces griseoluteus* ISP 5392 strain, a typical strain of *S. Griseoluteus*, was made and the results obtained are shown in Table 2 below.

Table 2

| | SF-1942 Strain | Streptomyces griseoluteus ISP 5392 |
|---|---|---|
| Morphology: | | |
| End of Aerial Mycelium | Linear | Mainly linear, but some mycelia are hook-like in shape. |
| Spore Surface | Smooth | Smooth |
| Culture Characteristics: | | |
| Glycerol-Asparagine Agar | Moderate growth. Reverse color is pale yellowish gray. Aerial mycelium is gray [e]. No spore formation | Moderate growth. Reverse color is pale grayish yellow. Aerial mycelium is white to grayish white. No spore formation. |
| Starch Agar | Fair growth. Reverse color is pinkish gray-brown. Aerial mycelium is abundant and gray [e-3ig]. No spore formation or pale grayish pink. | Fair growth. Reverse color is pinkish yellow-brown. Aerial mycelium is abundant and gray [e-3ig]. No spore formation or slightly reddish gray-yellow. |
| Yeast Malt Agar | Scant to moderate growth. Reverse color is pale yellow. No aerial mycelium. No spore formation. | Moderate growth. Reverse color is grayish yellow. Aerial mycelium is gray [3ig]. No spore formation. |
| Tyrosine Agar | Fair growth. Reverse color is brown. Aerial mycelium is abundant and gray [e]. No spore formation. | Fair growth. Reverse color is brown. Aerial mycelium is abundant and gray [e]. No spore formation. |
| Production of Melamine-like Pigments | Negative | Negative |
| Utilization of Carbon Sources | | |
| D-Fructose | + | + |
| D-Xylose | + | + |
| D-Mannitol | + | + |
| D-Inositol | + | − |
| L-Arabinose | + | + |
| Rhamnose | − | − |
| Sucrose | + | − |
| Raffinose | + | − |
| Antibiotic Production | SF-1942 Substance | Griseolutein* |

*Griseolutein is a yellow to orange-yellow substance and is clearly distinguished from SF-1942 substance from the standpoint of their physical and chemical properties.

As is apparent from the comparisons shown in Table 2 above, SF-1942 strain compares with *Streptomyces griseoluteus*, though these strains are slightly different in some culture characteristics and utilization of some carbon sources.

Similar to other strains of the genus Streptomyces, the SF-1942 strain used in the present invention varies easily in its properties. Variation can be caused artificially by irradiation with, for example, UV light, X-rays, highfrequency waves or radioactive rays and chemicals. Therefore, all variants as well as mutants can be used in the process of this invention so long as such variants and mutants of the genus *Streptomyces* have the ability to produce the SF-1942 substance.

According to the process of this invention, the above-described strains can be cultivated in a medium containing the nutrients which are assimilable by known microorganisms. The nutrient sources can be known materials such as carbon sources, nitrogen sources, minerals, etc. conventionally used in the cultivation of strains of the genus Streptomyces. Examples of carbon sources which can be used are glucose, sucrose, starch, glycerin, millet jelly, molasses, soybean oil, etc. Examples of nitrogen sources which can be used are soybean powder, wheat germ, meat extract, peptone, dry yeast, corn steep liquor, ammonium sulfate, sodium nitrate, etc. Additionally, inorganic salts such as calcium carbonate, sodium chloride, potassium chloride, phosphates, etc., as well as those organic and inorganic materials that enhance microbial growth and the production of the desired SF-1942 substance can be advantageously incorporated into the culture medium if required.

For cultivation, as with the ordinary production of antibiotics, liquid culture, especially submerged culture is most suitable. The cultivation can be effected under aerated conditions at an optimal temperature of about 22° to about 32° C., preferably around 28° C. The production of the SF-1942 substance reaches a maximum in about 2 to about 6 days in both shake-culture and tank-culture.

The SF-1942 substance obtained in accordance with the process of this invention is a neutral antibiotic substance which does not contain nitrogen. In isolating the SF-1942 substance from the fermentation broth, care should be taken in the chemical and physical properties of the SF-1942 substance which are described hereinafter in detail. The isolation of the SF-1942 substance can be achieved using conventional isolation and purification techniques, for example, filtration of the fermentation broth, extraction of the filtrate, purification by column chromatography, etc., using ion-exchange resins such as Amberlite XAD-2 (a tradename, produced by Rohm & Haas Co., U.S.A.), Diaion HP-20 (a tradename, produced by Mitsubishi Chemical Industries, Ltd., Japan) and the like, adsorbents, such as activated carbon, alumina and the like, gel filter aids such as Sephadex G-10 and Sephadex LH-20 (a tradename, produced by Pharmacia Co., Sweden), precipitation by hexane, solvent extraction using ethyl acetate, silica gel chromatography and the like.

A typical embodiment which can be advantageously used for the isolation and purification of the SF-1942 substance is described in detail below.

The pH of the fermentation broth is first adjusted to a pH of 2.0 with hydrochloric acid and then microbial cells and any solid materials contained in the broth are removed by filtration using a filter aid such as diatomaceous earth. The active ingredient in the filtrate is then extracted with a solvent such as ethyl acetate, and the extract is concentrated under reduced pressure to dryness thereby removing the ethyl acetate. Diethyl ether is added to the residue and any insoluble materials are removed. n-Hexane is then added to the ethereal solution in a volume of about 15 times the volume of the ethereal solution, and the mixture is cooled with ice to precipitate the active substance. The precipitated active substance is dissolved in a small amount of ethyl acetate, and the resulting solution is charged into a column packed with activated carbon which has been charged with ethyl acetate. The column is then eluted with ethyl acetate to obtain active fractions containing the SF-1942 substance. The active fractions are finally purified using an appropriate combination of column chromatographic purification procedures using silica gel (eluted with a mixture of chloroform-methanol, 50:1 by volume and then a mixture of benzene-acetone, 15:1 by volume), Sephadex LH-20, Sephadex G-10, etc. to obtain the SF-1942 substance having a high purity.

The bioassay of the SF-1942 substance can be performed as described in detail below.

The assay medium (pH 7.0) was composed of 0.5% polypeptone, 0.3% meat extract, and 1.5% agar. *Bacillus subtilis* PCI-219 strain was used as the test organism. The results obtained indicate that within the concentration range of 12 mcg/ml to 3 mcg/ml of the SF-1942 substance, a linear relationship exists between the logarithm of the concentration and the diameter of inhibition zones having a diameter of from 22.8 to 12.4 mm (paper disc method).

The physical and chemical properties of the SF-1942 substance are set forth below.

Figure 2:
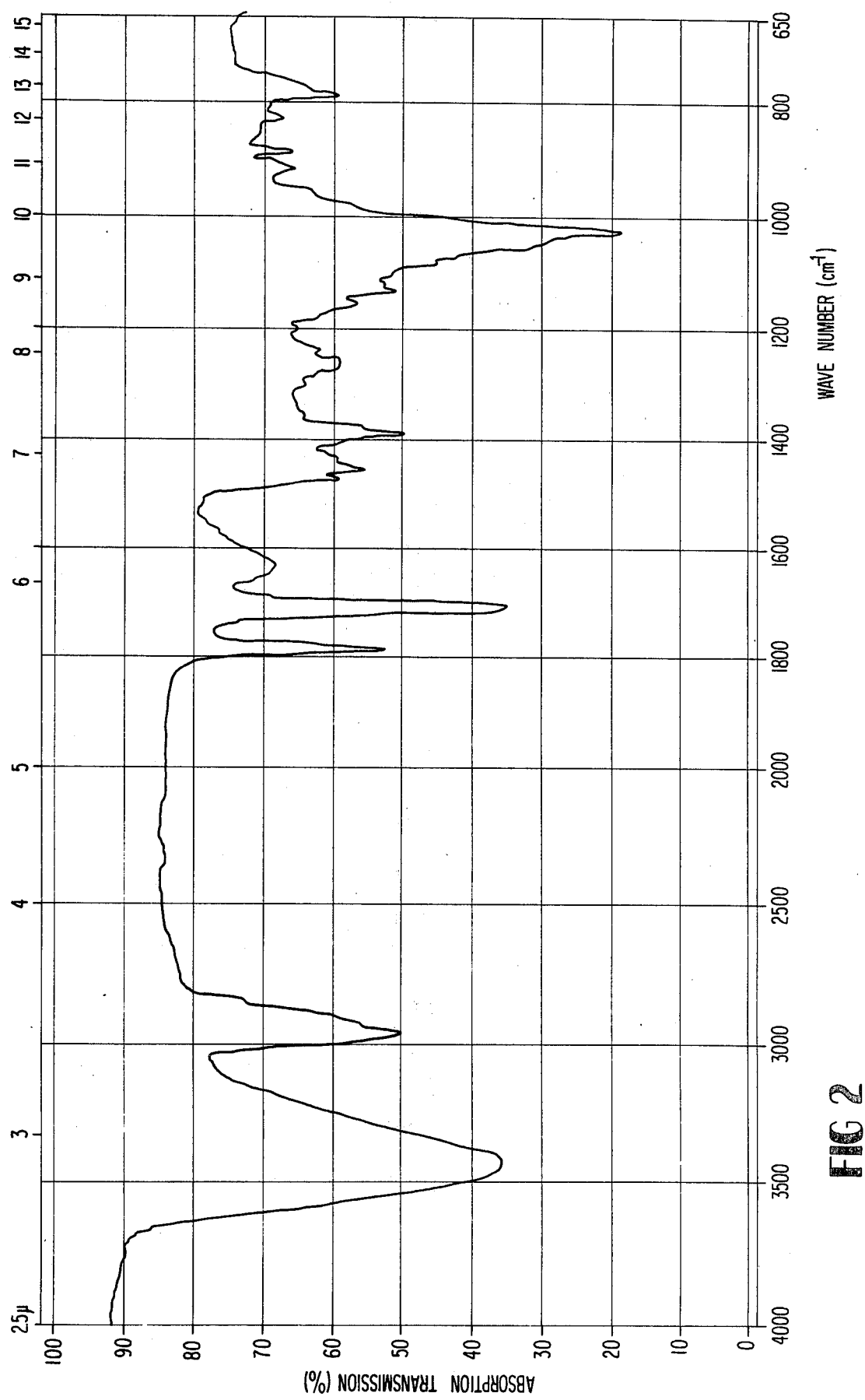
FIG. 2 is an infrared absorption spectrum of the SF-1942 substance as determined in a KBr tablet.

(1) Appearance: White amorphous powder;
(2) Decomposition Point: Indefinite, but the volume of the sample begins to decrease at about 122° C., turns brown at about 134° C. and gradually decomposes.
(3) Elemental Analysis: C: 65.57%; H: 7.80%; O: 26.38%; N: 0%.
(4) U.V. Absorption Spectrum: The spectrum as determined in methanol is shown in FIG. 1 and no characteristic maximum absorptions are found between the wavelength of 350 to 210 mm.
(5) I.R. Absorption Spectrum: The absorption spectrum, as determined using the KBr tablet method, is shown in FIG. 2 with absorption bands at 3400, 2960, 1780, 1710, 1630, 1450, 1390, 1020, 780 cm$^{-1}$.
(6) Molecular Weight: 350 to 400 as determined by the vapor pressure method;
(7) Optical Rotation $[\alpha]_D$: $-21.8°$, 1% methanol solution.
(8) Solubility: Soluble in ethyl acetate, lower alcohols ($C_1$–$C_3$), benzene, diethyl ether, acetone and chloroform, and insoluble in water and hexane;
(9) Color Reactions: Positive in color reactions with Lemieux, sulfuric acid and 2,4-dinitrophenylhydrazine, and negative in color reactions with ninhydrin and Greig-Rayback reagent;
(10) Stability: Stable at an acidic pH, relatively unstable at a neutral pH and very unstable at an alkaline pH;
(11) Rf Value on Silica Gel Thin Layer Chromatography (Coloring with Lemieux);

| Elution Solvent System | Rf Value |
| --- | --- |
| Benzene-Methanol (5:1 by volume) | 0.52 |
| Chloroform-Methanol (10:1 by volume) | 0.46 |
| Benzene-Acetone (2:1 by volume) | 0.41 |

(12) High voltage electrophoresis using filter paper (3000 V, 15 min., pyridine-acetate buffer of pH 6.4): Alanine (comparison compound) migrated 2.1 cm toward the anode and, the SF-1942 substance migrated 1.4 cm toward the anod. Therefore, the SF-1942 substance is electrically neutral.

The antibiotic activities of the SF-1942 substance against various organisms are shown in Table 3 below.

Table 3

| Antimicrobial Spectrum of SF-1942 Substance | |
| --- | --- |
| Test Organism | M.I.C. (mcg/ml)* |
| *Bacillus subtilis* PCI-219 | 0.1 |
| *Staphylococcus aureus* 209P | 0.2 |
| *Sarcina lutea* | 0.05 |
| *Escherichia coli* | 6.25 |
| *Escherichia coli* K-12-R | 6.25 |
| *Pseudomonas aeruginosa* | 6.25 |
| *Klebsiella pneumoniae* | 12.5 |
| *Vibrio percolens* | 0.78 |
| *Salmonella typhi* | 1.56 |
| *Proteus vulgaris* | 1.56 |
| *Mycobacterium smegmatis* 607 (Km-R) | 12.5 |

*The minimum inhibitory concentration (M.I.C.) was determined on a heart infusion agar medium.

As is apparent from the results in Table 3 above, the SF-1942 substance exhibits broad and potent antimicrobial activities against Gram-positive and Gram-negative bacteria.

The acute toxicity of the SF-1942 substance was also determined in mice (5 mice per group) and, as a result of observation for 7 days after intraperitoneal administration of the SF-1942 substance at a dose of 3 mg/Kg, two mice died.

The antitumor activity of the SF-1942 was determined using Sarcoma 180. Sarcoma 180 tumor cells ($11.4 \times 10^6/0.06$ ml) were intraperitoneally transplanted in each mouse (ICR strain, about 8-weeks old, 5 mice per group) and 24 hours after the transplantation, the SF-1942 substance was intraperitoneally administered to each mouse for 3 consecutive days at a dose of 4 mg/Kg, 2 mg/Kg, 1 mg/Kg or 0.5 mg/Kg. Thereafter, the average survival time (days), the percent prolongation of life and the amount of abdominal dropsy were determined and the results obtained are shown in Table 4 below.

Table 4

| Antitumor Activity of SF-1942 Substance Against Sarcoma 180 | | | | |
| --- | --- | --- | --- | --- |
| Dose (mg/kg) | Average Survival (days) | Prolongation of life (%) | Amount of Abdominal Dropsy (ml) | Survival Number (after 60 days) |
| 4 | 26.4 | 8.2 | 0 | 0/5 |
| 2 | 53.0 | >117.2 | 4.6 | 4/5 |
| 1 | 48.8 | >100.0 | 10.8 | 3/5 |
| 0.5 | 45.0 | >84.4 | 1.0 | 3/5 |
| 0 | 24.4 | — | 20.8 | 0/5 |

As shown by the results in Table 4 above, the SF-1942 substance of this invention exhibits an antitumor activity against Sarcoma 180 at a relatively low concentration (4–0.5 mg/Kg). The SF-1942 substance is expected to be useful using either intramuscular or subcutaneous administration.

The present invention is further illustrated in greater detail by the following Example, but the example is not to be construed as limiting the present invention. Unless otherwise indicated, all parts, percentages, ratios and the like are by weight.

EXAMPLE

(1) Cultivation of SF-1942 Strain

Cultivation was conducted using Streptomyces sp. SF-1942 strain (FERM P-3939) as a seed culture and a seed medium comprising 2.0% soluble starch, 1.0% polypeptone, 0.3% beaf extract and 0.05% $K_2HPO_4$ (pH before sterilization; 7.0).

Each of 5 seed media (b 100 ml) having the above composition in a 500 ml-Sakaguchi flask was inoculated with one platinum-loop full of the above seed culture and then culturing was at a temperature of 28° C. for 48 hours. Then 20 l of a seed medium having the same composition as above in a 30 l jar fermentor was inoculated with the resulting seed culture (500 ml) and cultured at a temperature of 28° C. for 24 hours with aeration and stirring.

200 l of a large scale production medium comprising 2.5% glucose, 2.5% Fermamedia (tradename, produced by Traders Oil Mill Co.), 0.25% sodium chloride (pH before sterilization; 7.0) in a 300 l-fermentor was then inoculated with the resulting seed culture (20 l), and then cultured at a temperature of 28° C. for 48 hours with aeration and stirring.

After completion of the culturing, the pH of the fermentation broth was adjusted to a pH of 2.0 with 6N hydrochloric acid and the fermentation broth was filtered using diatomaceous earth as a filter aid to obtain about 170 l of a filtrate. (2) 100 l of ethyl acetate was then added to 170 l of the filtrate obtained as described above and the mixture was stirred for about 2 hours to extract the active substance into the ethyl acetate layer. The separated ethyl acetate layer was concentrated to a volume of 2 l under reduced pressure, washed with water (pH 2.0) and concentrated to obtain about 65 g of a syrup.

500 ml of diethyl ether was added to the resulting syrup and any insoluble material was removed using a glass filter followed by concentration of the filtrate to a volume of about 100 ml. 1.5 l of n-hexane was added to the concentrate and the mixture was cooled with ice to precipitate a product (32 g; purity, 2 to 3%).

The resulting product was then charged into a column of activated carbon filled with ethyl acetate and the column was eluted with ethyl acetate whereby an active substance began to be eluted in a fraction from about 1.5 to 6 times the volume of the activated carbon (500 cc). The active fraction was then concentrated under reduced pressure and the concentrate was charged into a column packed with 800 ml of silica gel. The column was eluted with a mixture of chloroform and methanol (50:1 by volume) to obtain active fractions 60 to 158 (18 ml in each fraction).

The pooled active fractions were concentrated under reduced pressure and the resulting concentrate was charged into a column packed with 600 ml of silica gel. The column was then eluted with a mixture of benzene and acetone (15:1 by volume) to obtain active fractions 30 to 145 (18 ml in each fraction). The period active fractions were then concentrated under reduced pressure to obtain 9.4 g of a brown syrup containing the SF-1942 substance (purity, about 7 to 8%). (3) 4 g of the crude SF-1942 substance obtained as described above was dissolved in 4 ml of methanol, and the solution was charged into a column packed with 800 ml of Sephadex LH-20. The column was then eluted with 20% aqueous methanol to obtain active fractions 74-192 (10 g in each fraction).

The pooled fractions were then concentrated under reduced pressure to remove methanol and, after the precipitated insoluble material was removed, the active substance was extracted with ethyl acetate. The extract was concentrated to dryness under reduced pressure to obtain about 900 mg of a crude yellow brown powder containing the SF-1942 substance. The resulting powder was dissolved in methanol and the solution was passed through a column packed with 800 ml of Sephadex LH-20 in the same manner as described above.

The column was then eluted with 20% aqueous methanol to obtain active fractions 56 to 72 (15 ml in each fraction). The pooled fractions were concentrated under reduced pressure and the concentrate was lyophilized to obtain 110 mg of the SF-1942 substance as a white powder.

While the invention has been described in detail and with reference to specific embodiments thereof, it will be apparent to one skilled in the art that various changes and modifications can be made therein without departing from the spirit and scope thereof.

What is claimed is:

1. An antibiotic SF-1942 substance having the following properties:

Appearance and Nature: White and electrically neutral substance;

Decomposition Point: Gradually melts over a temperature range of from 122° to 134° C. with decomposition (amorphous powder);

Elemental Analysis (by weight): C: 65.57%; H: 7.80%; O: 26.38%; N: 0%;

U.V. Absorption Spectrum: No characteristic maximum U.V. absorption;

I.R. Absorption Spectrum: Absorption bands at 3400, 2960, 1780, 1710, 1630, 1450, 1390, 1020, 780 cm$^{-1}$ and absorption spectrum as shown in FIG. 2 as determined using the KBr tablet method;

Optical Rotation: $[\alpha]_D^{20} = -21.8°$, 1% methanol solution;

Molecular Weight: 350 to 400 as determined by the vapor pressure method;

Solubility: Soluble in ethyl acetate, lower alcohols ($C_1$–$C_3$), acetone, benzene and chloroform, and insoluble in water and hexane;

Color Reactions: Positive, Lemieux, sulfuric acid, and 2,4-dinitrophenylhydrazine; Negative, ninhydrin and Greig-Rayback reagent.

Rf Values on TLC (Silica Gel): 0.52 (benzene/methanol; 5:1 by volume) 0.46 (chloroform/methanol; 10:1 by volume) 0.41 (benzene/acetone; 2:1 by volume)

Mobility on Filter Paper High Voltage Electrophoresis: Behaves as electrically neutral substance.

2. A process for preparing an antibiotic SF-1942 substance from Streptomyces sp. SF-1942, or a SF-1942 substance producing variant or mutant thereof, which comprises cultivating Streptomyces sp. SF-1942, or said variant or mutant thereof, in a nutrient medium containing assimilable carbon and nitrogen sources at a temperature of about 22° to about 32° under aerobic conditions until a substantial amount of said SD-1942 substance is accumulated in said nutrient medium, and recovering said SF-1942 substance from the nutrient medium.

* * * * *